(12) United States Patent
De Gregorio

(10) Patent No.: US 6,342,255 B1
(45) Date of Patent: Jan. 29, 2002

(54) TOPICAL PHARMACEUTICAL COMPOSITIONS USEFUL FOR THE TREATMENT OF CUTANEOUS OF CIRCULATORY PATHOLOGIES ON INFLAMMATORY, IMMUNE, PROLIFERATIVE OF DEGENERATIVE BASIS

(75) Inventor: Chiara De Gregorio, Cori (IT)

(73) Assignee: Codex V s.r.l., Cori (IT)

( * ) Notice: Subject to any disclaimer, the term of this patent is extended or adjusted under 35 U.S.C. 154(b) by 0 days.

(21) Appl. No.: 09/700,118

(22) PCT Filed: May 12, 1999

(86) PCT No.: PCT/EP99/03289

§ 371 Date: Nov. 13, 2000

§ 102(e) Date: Nov. 13, 2000

(87) PCT Pub. No.: WO99/59523

PCT Pub. Date: Nov. 25, 1999

(30) Foreign Application Priority Data

Sep. 15, 1998 (IT) ......................... MA98A1073

(51) Int. Cl.⁷ ............................... A61K 35/78
(52) U.S. Cl. ...................... 424/778; 424/539; 424/725; 424/750; 424/757; 424/778
(58) Field of Search ............... 424/778, 539, 424/725, 750, 757

(56) References Cited

U.S. PATENT DOCUMENTS 5,100,672 A * 3/1992 Gueret et al.
5,118,507 A * 6/1992 Clement
5,855,893 A * 1/1999 Weinkauf et al.
5,869,708 A * 2/1999 Das et al.
6,146,616 A * 11/2000 Msika et al.

FOREIGN PATENT DOCUMENTS

| EP | 0 279 135 A3 | 12/1987 |
| EP | 0 279 136 A2 | 12/1987 |
| EP | 0 499 015 A1 | 6/1991 |
| EP | 0 521 647 A2 | 6/1992 |
| EP | 0 858 799 A2 | 8/1998 |
| EP | 0 858 799 A3 | 8/1998 |
| FR | 2142194 | 1/1973 |
| FR | 2 324 293 | 4/1977 |
| WO | WO 98/05294 | 2/1998 |
| WO | WO 98/06714 | 2/1998 |

OTHER PUBLICATIONS

Giorgio Rialdi et al., XP–002119893, "Assessment on the Biological Activity on Filaggrin by a Natural Derivatives for Skin Care Applications", Scientific and Medicine Dept. 1993, vol. IV In Cosmetic Conf. pp 45–52.

XP–002119894, "Creme De Nuit Anti–Age", France World Contacts Tradings Ltd., 1996—From Website www.france-contacts.com, one page.

Dominique Parent et al., XP–002119895, "Spreading of Psoriatic Plaques: Alteration of Epidermal Differentiation Precedes Capillary Leakiness and Anomalies in Vascular Morphology", Experimental Dermatology Unit et al. J. Invest. Derm. vol. 95(3) pp 333–340 1990.

* cited by examiner

Primary Examiner—Christopher R. Tate
(74) Attorney, Agent, or Firm—Young & Thompson

(57) ABSTRACT

Topical pharmaceutical compositions, containing as active ingredient a mixture of pollen extracts and vegetable oil unsaponifiables, useful for the treatment of cutaneous or circulatory pathologies on inflammatory, immune, proliferative or degenerative basis.

7 Claims, No Drawings

TOPICAL PHARMACEUTICAL COMPOSITIONS USEFUL FOR THE TREATMENT OF CUTANEOUS OF CIRCULATORY PATHOLOGIES ON INFLAMMATORY, IMMUNE, PROLIFERATIVE OF DEGENERATIVE BASIS

The present invention relates to pharmaceutical topical compositions containing pollen extracts and unsaponifiable fractions of vegetable oils for the treatment of cutaneous or circulatory pathologies on inflammatory, immune, proliferative or degenerative basis.

One of the problems of all cutaneous chronic inflammatory pathologies, when the etiological agent causing the inflammatory process itself cannot be removed, is the control of the inflammatory process and the reactivation of the tissue trophism. Chronic inflammatory processes are generally associated with severe dystrophism of the affected tissue, which is mainly related to the impairment of the efficiency of the tissue microcircle (permanent dilation of capillaries and venules with alterations of capillary permeability). When the inflammatory event is on an immunopathogenic basis, said process becomes chronic mainly as a consequence of a persistent alteration of the mutual regulation of the various components of the immune system and/or of cytochemical signals. On the other hand, each inflammatory process on immunopathogenic basis is expected to have a determined duration and naturally end when the exogenous noxae or the "non-self" elements which have triggered the immune process have been eliminated and the involved lymphocytes have undergone apoptosis death.

When the cause which has triggered the disease cannot be removed, the following therapeutical objectives should be attained:
1) control of the chronic inflammatory reaction by modulating self-regulation unbalances of the immune system, also through pharmacological stimulation of any poorly active immunocompetent cells;
2) direct reactivation of tissue trophism by acting on microcircle and on non-immunocompetent cells directly responsible for functionality and well-being of the tissue itself, which are generally involved in the damages related to the inflammatory reaction.

Said objectives are fundamental in case of both cutaneous and systemic, inflammatory pathologies. Therefore, a medicament exerting the above mentioned action on cutaneous pathologies could also be used in the case of systemic pathologies by means of a suitably formulated transdermal system. At present the available medicaments comprise steroidal or nonsteroidal, topical or systemic, immunosuppressors. On the other hand, the long-term topical and systemic side-effects of corticosteroids on tissue trophism are well known. Immunosuppressors such as cyclosporin have in their turn precise limits of use. Very few nonsteroidal anti-inflammatory drugs are useful to some extent in cutaneous chronic inflammatory pathologies, in that they are poorly active and induce pharmacological tolerance to the antiinflammatory action, even after short times. According to the available knowledge, wide-spectrum immunomodulators are known to induce no pharmacological tolerance to the antiinflammatory effect, while exerting a direct reactivation of cutaneous trophism, nor substances exerting a strong trophic effect in physiological conditions as well as an immunomodulating effect in pathological conditions, thanks to their vasoactive and vasogenic actions.

It has now unexpectedly been found that the combination of pollen extracts with vegetable oil unsaponifiables, administered topically, provides advantageous therapeutical results which are surprisingly resolutive in the treatment of the skin pathologies. This means that the topical formulations comprising said combination not only have a lenitive or symptomatic pharmacological activity, but also can cause, in a high number of cases, the even complete remission of the pathology, without relapses after the treatment has been interrupted.

The pollen extract is a complex mixture of natural substances and nutrients which has been used in the cosmetic art, thanks to its emollient and restitutive properties, in combination with other active principles having similar or complementary activity. Pollen extract is commercially available (see, for example, G. Proserpio, A. Malpede, A. M. Massera, Fitocosmetopea Sinerga, Sinerga Ed. 1995; CTFA Buyer's Guide) and it essentially comprises a mixture of protides (10–35%), glucides (15–40%), lipids (1–10%), salts, oligoelements, vitamins and a water content from 10 to 20%. It further contains a series of $C_{27}$, $C_{26}$ and $C_{29}$-sterols, as reported in Phytochemistry, 1968, Vol. 7, 1361–1365.

Pollen extract also has a series of further applications, generally related to the well-being of the body and of course depending on the type of extraction process as well as on the purity degree or concentration obtained.

In fact, being a natural nutrient, it is added to foodstuff intended for the improvement of psychophysical conditions in humans. For example, CN 1100599 describes a concentrate of pollen extracts for fighting fatigue and mental uneasiness. Similarly, KR 9400320, SU 1660668, EP 87669 disclose the alimentary use of pollen extracts in combination with other nutrients.

One widespread use of pollen extract is anyway in the cosmetic field, as active component with adjuvating action, generally in formulation with other active principles, excipients and carriers known in the art and useful for the intended purpose. Thus, for example, U.S. Pat. No. 4737360 discloses skin care compositions comprising a pollen extract and a blend of natural oils as carriers to increase skin permeability. Also JP 52090635, JP 6287106, RU 2054926, SU 1806736, SU 1785684, SU 1734751, SU 1713555, SU 1683750; SU 1597192, FR 2631824, FR 2597337, SU 992057 disclose formulations for the cosmetic use, mainly as face-creams, in which pollen extracts are mixed with a series of skin protective or nutritive components.

Pollen extracts are also used in the preparation of toilets soaps (SU 1691390, SU 1618759), tooth-pastes (SU 1007671), lipsticks (SU 1486167), hair-care compositions (RU 2072831, SU 997681).

It has also been described, albeit not very often, a potential use of pollen extract as a complement or supplement of pharmacological treatments in various allergic (EP 201053, JP 5076597), tumor (EP 220453, U.S. Pat. No. 5,744,187), infective (RU 2090198), inflammatory (FR 2142194, RO 80826, JP 9278665, CN 8603867) pathologies, as well as in other pharmaceutical applications (CH 381358, EP 499015, U.S. Pat. No. 3,906,092).

Conversely, no specific pharmacological properties or activities are known, ascribable to the unsaponifiable fraction obtainable from vegetable oils, such as olive, soybean, wheat germ, sunflower, avocado, sesame, almond, safflower, carrot seeds, peanut, hazelnut, castor oils and the like. Said oils are used per se in the alimentary field, as well as carriers, excipients, binders in topical cosmetic or pharmaceutical formulations, such as oils, gel, creams, pastes and the like.

The unsaponifiable fractions of said vegetable oils are a minimum percentage (0.5 to 3.5%) and substantially consist of mixtures of carotenoids, branched hydrocarbons, flavonoids, phytosterols and other products having a complex, still partially unknown structure.

Likewise, no combinations of pollen extracts with significant amounts of vegetable oil unsaponifiables, preferably of olive, soybean and wheat germ oils, are known, having pharmacological properties, in particular therapeutical activity on cutaneous or circulatory pathologies of various origin.

It has now unexpectedly been found that formulations comprising as active ingredient a combination of pollen extracts and vegetable oil unsaponifiables, optionally in combination with other active principles with adjuvating, complementary or supplementing activity, exert a potent, often resolutive therapeutical action in many different affections of the skin.

The formulations of the present invention, in particular those for the topical use, can unexpectedly modulate the vascularization of dermal tissues.

"Modulation of the vascularization" means the ability to restore the activity and efficiency of microcircle, when it has been impaired by conditions causing either its excessive (in chronic inflammatory conditions, psoriasis, etc.), or its insufficient (in senescence, dermal atrophy, etc.) development, with consequent hypervascularization or insufficient vascularization.

In fact, the formulations of the invention proved to be active both in limiting and controlling the hypervascularization characteristic of chronic inflammatory conditions, and in activating microcircle when it is inefficient or reduced due to various causes.

The effect on microcircle is therefore due to this balancing activity. The experimental results have, in fact, evidenced that, independently of the cause of microcircle inefficiency (such as chronic inflammatory conditions, alteration of large venous vessels, venous insufficiency in lower limbs, tissue dystrophy or atrophy due to hormonal insufficiency, senescence, and the like), the formulations of the invention prevent degeneration of microcircle functionality, restoring its natural equilibrium (modulating action).

It has also unexpectedly been found that the modulating action on microvessels is combined with a wide-spectrum immunomodulation action on all immuno pathogenic mechanisms. Said effect resolves the inflammatory component, whether it is the cause of microcircle impairment or a parallel event.

Furthermore, the formulations of the invention, thanks to their modulating action on microcircle, show a high penetration into the deep layers of the skin, acting as a particularly effective transdermal system, attaining therefore the non-symptomatic resolution of chronic pathologies. For example, complete resolution of psoriasic plaques has been obtained, in cases of vulgaris chronic psoriasis localized in limited, rapid-absorption areas. Observation after one-month treatment evidenced the disappearance of the lesion and the onset of repigmentation of the area from the edges to the centre. After two-month treatment neither signs of the preceding lesion nor dyschromic areas were observed. The skin had an healthy, repigmentated appearance and the capillaroscopic pattern was similar to that of healthy skin. The treatment was carried out for a further month, thus equilibrating the concerned area and avoiding relapses.

As a consequence of the features described above, the topical compositions of the invention also exert a strong trophic action on the skin, as they have high moisturizing power, keratoplastic effect due to keratinization equilibrating activity and peripheral sebomodulating action.

The formulations of the invention are also useful in the treatment of skin ageing, microtelangiectasias and couperose, dystrophic skin (also as a consequence of pharmacological treatments, for example with corticosteroids). Furthermore, they are also useful in the moisturizing and sebomodulating treatment of acne and seborrheic conditions, in that they act through a peripheral mechanism not involving the systemic transit. They also exert a moderate peripheral antiinflammatory action together with a trophic and moisturizing effect on the skin, contrary to the known antiinflammatories.

The formulations of the invention are also very effective in the antiage treatment of the skin, in that they exert a real action on skin ageing, acting on all the affected parameters (such as vascularization, which decreases in time), and not only the adjuvant, antilipoperoxidative or moisturizing actions typical of cosmetic compositions. These formulations increase skin microcircle vascularization, therefore significantly improving trophism as well as superficial and deep hydration, while arresting radicalic lipoperoxidation. The obtained results also depend on the duration of the treatment, also as for long-term effects.

According to the invention, the pollen extract is mixed with one or more unsaponifiable fractions of vegetable oils, preferably selected from those obtained from olive, soybean or wheat germ oils.

The pollen extract : vegetable oil unsaponifiables weight ratio is not critical, but it usually ranges from 10:1 to 1:10, preferably about 1:1.

The mixture of pollen extract and vegetable oil unsaponifiables is formulated according to the invention preferably in suitable topical administration forms using conventional excipients. Examples of said formulations comprise creams, ointments, lotions, gels, oils, gel-oils, ointments, gauzes or medicated patches and the like. The mixture of pollen extract and vegetable oil unsaponifiables, although per se having a very good transdermal penetration, can optionally be formulated in a matrix suitable for the transdermal administration.

The compositions of the invention can optionally contain further active principles with adjuvating, complementary or supplementing activities or anyway useful for the therapeutical use. Thus they will contain, for example, zinc oxide, salicylates, collagene, heparinoids and the like.

Isodecyl-ortho-hydroxy-benzoate (isodecylsalicylate) and zinc oxide are particularly preferred.

The weight percentage of the mixture of pollen extract and unsaponifiables is not critical and can range within wide limits, in line with the chemical-physical characteristics of the pharmaceutical formulation. Generally speaking, said percentage will be preferably above 6%, more preferably from 6 to 25% about.

Non limiting examples of cutaneous pathologies on inflammatory, proliferative, immune or degenerative basis which can be treated by means of the topical compositions of the invention comprise chronic dermatitis (atopic, radiodermitis, dyshidrosis, lichenified eczema, allergic and seborrheic dermatitis, etc.); psoriasis and similar parakeratosic conditions; capillaritis, venulitis, vasculitis in general and angiodermitis; Bateman dermatitis; pyodermitis; rosacea; viral pathologies (such as herpes labialis, herpes zoster and Papilloma virus warts; stasis, elderly and obese dermatitis, post-peeling dermatitis, decubitus erythema; telangiectasias.

The compositions of the invention are also useful in the treatment of skin or circulation pathologies characterized by cell hyperproliferation, such as actinic dyskeratosis and epitheliomas, and exert strong systemic effects in the treatment of chronic venous insufficiency of lower limbs, thanks to their wide-spectrum immunomodulating, vasoactive and vasokinetic characteristics, which induce rapid cicatrization of venous ulcers, reduction in stasis eczema and lymphedema and inhibition of formation of dyschromic events related to these pathologies.

Furthermore, the combinations of the invention are useful in the treatment of pathologies such as arteritis, which require transdermal administration.

Particularly advantageous effects are obtained in irritative dermatitis, dyshidrosis, seborrheic dermatitis, radiodermatitis following radiotherapy in tumor post-surgery, rosacea, capillaritis, venulitis and angiodermitis.

Beneficial effects are also observed in the treatment of actinic dyskeratosis lesions following surgery. Interestingly, patients treated with the formulations of the invention showed no relapses.

Treatment of epitheliomas induced very good cicatrization of the lesions, so that no disruptive surgery such as amputations and the like was needed.

Spots from treatments with sclerosing agents, as well as nipple fissures, anus fissures, hemorrhoids, neo-formed pink stretch marks, can also be treated with very good results.

The compositions of the invention can be administered for prolonged times, usually from a few weeks to some months, once or more times a day, preferably at least twice a day.

The following examples further illustrate in detail the invention.

EXAMPLE 1

| | |
|---|---|
| Pollen extract | 5% |
| Wheat germ oil unsaponifiables | 2% |
| Olive oil unsaponifiables | 2% |
| Soybean oil unsaponifiables | 1% |
| Linolenate | 3% |
| Isodecylsalicylate | 12% |
| Carriers for formulating a cream, gel, paste, | q.s. to 100%. |

EXAMPLE 2

| | |
|---|---|
| Pollen extract | 5% |
| Wheat germ, olive and soy-bean unsaponifiables | 5% |
| Zinc oxide | 10% |
| Carriers | q.s. to 100% |

EXAMPLE 3

| | |
|---|---|
| Pollen extract | 5% |
| Wheat germ, olive and soy-bean unsaponifiables in lipogel carrier | 3% |

EXAMPLE 4

The therapeutical effectiveness of the preparations of the Examples 1 and 2 in the treatment of atopic dermatitis and irritative dermatitis of hands, resistant to any other treatment, was evaluated. A similar evaluation was carried out on patients affected with telangiectasias.

Tests were performed on 28 patients of both sexes, respectively with:

| | |
|---|---|
| atopic dermatitis | No. 10 patients |
| irritative dermatitis of hands | No. 9 patients |
| telangiectasias | No. 9 patients |

Inclusion criteria: both sexes, age 35–65 years, absence of pathologies requiring therapies interfering in the evaluation of the results.

Exclusion criteria: pregnancy, breast feeding, use of contraceptives or steroidal antiinflammatories, patients with diabetes, endocrine, hepatic or renal diseases.

Each patient was kept under observation from the beginning of the protocol until the maximum therapeutical result which could be reached according to the dermatologist. At the end of the protocol, patients is were observed for a time during which self-medication was carried out discontinuously. Weekly controls were performed during the whole observation period. Improvement was evaluated according to a 5 semi quantitative score (−1=worsening; +3=maximum improvement reachable) and subjected to Friedman's test.

Treatment

Atopic Dermatitis

4 Pediatric patients (3–7 years) and 6 adult patients (21–28 years), one of which under treatment with cyclosporin, were treated. The formulation of Example 2 was used in the morning and that of Example 1 at night, every day for 15 days, then 3 times a week during long-term therapy. The patient treated with Cyclosporin was treated with the formulation of Example 2 in the morning and that of Example 1 at night for long-term therapy.

Irritative Dermatitis of Hands

9 Female patients (28–43 years) with chronic irritative dermatitis of hands resistant to usual treatments. Tests carried out before the study excluded contact allergic dermatitis. Patients were treated with the formulation of Example 1 in the morning and that of Example 2 at night, every day for one month, then three times a week during long-term therapy. 4 Female patients were used as controls, which were treated with a common moisturizing cream.

Telangiectasias

9 Female patients (11–67 years), suffering from face dermatosis of various severity (couperose, persistent erythrosis, rosacea, rhinophyma). Patients were treated in the morning and at night with the formulations of Examples 1 and 2 for three months. Capillaroscopic evaluation on the right and left zygomatic areas was carried out at 30× with Macroblitz probe (CIR) and Sony microcamera, using Dermavision software, at the beginning and at the end of the treatment.

Results

Atopic Dermatitis

At the end of the first 15-day treatment, all patients showed a marked improvement of both erythematous and xerosic lesions. 8 patients out of 10 showed an improvement higher than 70% and the remaining 2 an improvement higher than 40%. The cyclosporin patient showed a marked improvement of the lesions with reduction in all erythematous lesions and disappearance of the xerotic ones.

Irritative Dermatitis of Hands

At the end of the one-month treatment, all patients showed a marked improvement: 6 patients an improvement higher than 70%, and 3 from 40% to 70%. Even after 4-month intermittent therapy, results proved satisfactory. When treatment was interrupted, symptoms reappeared in a short time. 3 Patients out of 4 treated with the common moisturizing cream showed at the end of the treatment a poor improvement, lower than 40%, and 1 showed no improvement.

Telangiectasias

At the end of the treatment, the complete resolution of the disease was attained in five patients and a marked improvement in the remaining four.

EXAMPLE 5

The therapeutical efficacy of the formulation of Example 3 in the treatment of face warts. A female patient (21 years) with flat warts as well as filiform warts diffused on the face was treated twice a day with the formulation of Example 3.

After one-month treatment, observation evidenced the remarkable reduction of the filiform warts and the almost complete disappearance of flat warts.

The same treatment on a further 5 cases gave satisfactory results as well.

What is claimed is:

1. A method of restoring impaired activity and efficiency of a microcircle of dermal tissue in a patient suffering from a cutaneous or circulatory pathology, said method consisting of administering to said patient a topical or transdermal formulation, which comprises as active principle an effective amount of a mixture of pollen extract and unsaponifiable fractions of one or more vegetable oils in admixture with a dermatologically acceptable excipient.

2. The method according to claim 1, in which said vegetable oils are selected from the group consisting of olive oil, soybean oil and wheat germ oil.

3. The method according to claim 1, in which said formulation further comprises at least one of zinc oxide, salicylates, collagen and heparinoids.

4. The method according to claim 1, in which said formulation further comprises zinc oxide or isodecyl-ortho-hydroxy-benzoate.

5. The method according to claim 1, in which said cutaneous or circulatory pathologies are of inflammatory, immune, proliferative or degenerative basis.

6. The method according to claim 1, in which said pathology is chronic dermatitis; elderly and obese dermatitis; decubitus erythema; radiodermatitis; parakeratosic conditions; capillaritis; venulitis; vasculitis; angiodermitis; pyodermitis; dermiopodermitis; rosacea; couperose; herpes labialis; herpes zoster; Papilloma virus warts; microtelangiectasias; or telangiectasias.

7. The method according to claim 1, in which said pathology is also characterized by cell hyperproliferation, or is the result of chronic venous insufficiency of lower limbs.

* * * * *